United States Patent [19]

Martz

[11] Patent Number: 4,846,164
[45] Date of Patent: Jul. 11, 1989

[54] VAPOR PERMEABLE DRESSING

[76] Inventor: Joel D. Martz, 5 Sealy Dr., Lawrence, N.Y. 11559

[21] Appl. No.: 83,690

[22] Filed: Aug. 7, 1987

[51] Int. Cl.[4] .............................................. A61L 15/00
[52] U.S. Cl. .................................... 128/155; 128/156; 428/90; 604/304
[58] Field of Search .................... 128/155, 156, 335; 604/304, 307, 358; 428/89, 90, 97

[56] References Cited

U.S. PATENT DOCUMENTS

| | | | |
|---|---|---|---|
| Re. 31,886 | 5/1985 | Hodgson | 128/156 |
| 2,949,443 | 8/1960 | Merriam | 128/156 |
| 3,425,412 | 2/1969 | Pope | 128/156 |
| 3,459,579 | 8/1969 | Newman | 428/90 |
| 3,616,156 | 10/1971 | Scholl | 128/155 |
| 3,800,792 | 4/1974 | McKnight | 128/156 |
| 3,842,832 | 10/1974 | Wideman | 128/156 |
| 4,285,338 | 8/1981 | Lemelson | 128/155 |
| 4,390,387 | 6/1983 | Mahn | 428/90 |
| 4,413,621 | 11/1983 | McCracken | 128/156 |
| 4,485,809 | 12/1984 | Dellas | 128/156 |
| 4,556,066 | 12/1985 | Semrow | 128/640 |
| 4,596,738 | 6/1986 | Metcalfe | 128/156 |
| 4,598,004 | 7/1986 | Heinecke | 128/156 |
| 4,616,644 | 10/1986 | Saferstein et al. | 128/156 |
| 4,619,253 | 10/1986 | Anhauser | 128/156 |
| 4,641,643 | 2/1987 | Greer | 128/156 |
| 4,649,909 | 3/1987 | Thompson | 128/155 |
| 4,706,662 | 11/1987 | Thompson | 128/156 |

Primary Examiner—James C. Yeung
Attorney, Agent, or Firm—David M. Warren

[57] ABSTRACT

A water vapor permeable dressing, such as a surgical dressing, is constructed of a thin elastomeric transparent film which is protected by a layer of non-woven fabric, preferably a fabric of spun-bonded material. The fabric is sufficiently thin, elastic and fluffy to absorb stress of abrasive objects so as to protect the underlying film. Both the film and the protective fabric are sufficiently thin and compliant to allow the dressing to conform to the contours of the human body. Adhesive used in the dressing, for securing the film to a person's skin, as well as for securing the fabric to the film, are permeable to water vapor, The film and the adhesives are impermeable to liquid water, thereby to provide an effective shield for a wound against infection by outside bacteria.

30 Claims, 2 Drawing Sheets

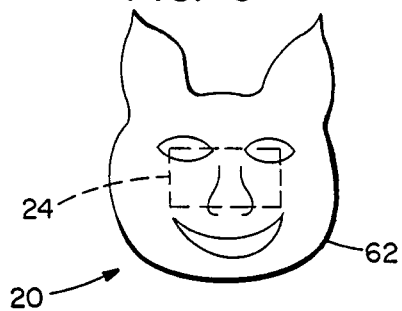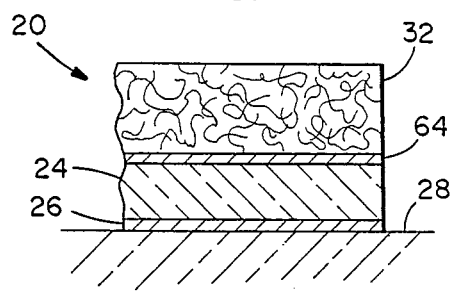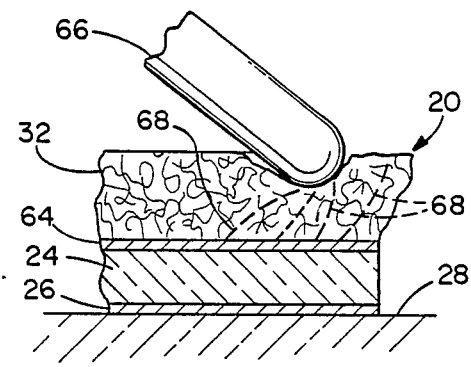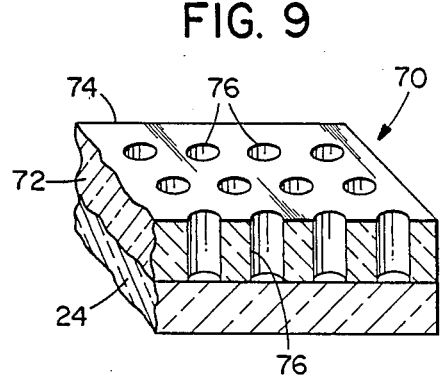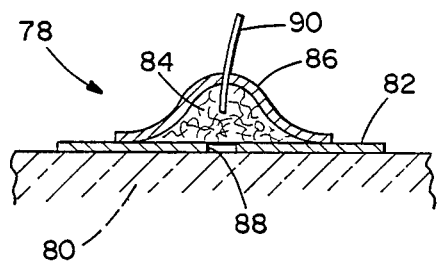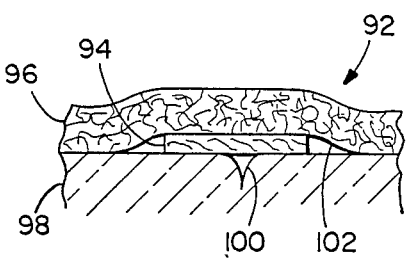

VAPOR PERMEABLE DRESSING

BACKGROUND OF THE INVENTION

This invention relates to moisture vapor permeable film dressings for covering wounds on human and animal skin, and, more particularly, to a structure of a thin transparent moisture vapor permeable film dressing with a moisture vapor permeable adhesive, there being a vapor permeable non-woven fabric secured to the film on a side opposite the adhesive to facilitate manipulation of the dressing, and to provide the thin film with protection from abrasion. The dressing may include optionally a pad on the adhesive side of the film for adsorption of body exudate. The composite structure of the film and the nonwoven fabric is sufficiently thin and elastic to readily conform to the shape of a body being draped by the dressing.

The use of thin films on the order of one mil thickness, which are impermeable to liquid water but permeable to water vapor is finding increased use in the construction of surgical dressings. Such dressings may include the film with or without a gauze pad or other absorptive plus some form of backing layer to facilitate emplacement of the dressing on the wound. Occasionally, the dressing is completed by use of gauze or other fabric which covers the film so as to protect the fragile film from abrasion and/or puncture by foreign objects which may contact the patient wearing the dressing.

The use of the thin film is advantageous for a number of reasons. The film is impermeable to liquid water and to bacteria so as to form a very effective shield which protects a patient from sources of infection external to the skin. The film retains body fluids within the body at the site of the wound. The vapor permeability of the film provides a sufficient rate of water vapor transport through the film to allow the skin to breathe normally. The film has sufficient elasticity to conform to the shape of various parts of the body, even a flexible body part such as a knee or elbow. Both the film and the adhesive layer may be constructed to be transparent, such transparency permitting the physician to observe the wound area without removal of the dressing. The material of the dressing is non-allergenic. The foregoing characteristics of the dressing permit the dressing to be kept in place for significantly longer periods of time than with other non-film types of dressings, this resulting in a great convenience to both the patient and attending medical staff, and also providing for better healing in some types of breaks in the integument, incisions, or wounds and providing better cost effectiveness in medical practice due to decreased need for dressing changes.

Such moisture vapor permeable films may be made from synthetic polymers and formed by casting, extrusion or other known film-making processes. Film thickness is in a range of typically 0.5–10 mils and preferably in a range from 0.6–3 mils. The film is continuous in that it has no perforations or pores which extend through the depth of the film. Films of this type are known and generally are hydrophyllic polymeric materials through which water vapor is capable of diffusing. The films are formed of plastic material such as polyurethane or acrylate copolymers, see McCracken et al, U.S. Pat. No. 4,413,621. A suitable adhesive for securing the thin film to human skin is disclosed in Hodgson, U.S. Pat. No. 3,645,835 (now U.S. Pat. Nos. Re. 31,886 and 31,887). Generally, these films have moisture vapor transport rates between 15 and 80 grams per 100 square inches per 24 hour interval at 100° Fahrenheit and 90% Relative Humidity.

In spite of the many advantages of the thin film, there are problems associated with its use. The film is too thin to be handled without some form of backing sheet or release sheet because the extreme flexibility and limpness allow the film to curl over upon itself. Furthermore, in the presence of an adhesive layer on one surface of the film, the film may stick to itself, this presenting great difficulty in applying the film to a patient. While the feature of transparency is most beneficial in allowing a physician to observe the wound, this feature is distressing to a patient who would prefer not to look at an ugly wound. The film, because of its extreme thiness, is fragile, and can readily catch on a sharp or rough object resulting in a tearing of a dressing constructed of the film.

If an attempt be made to overcome the foregoing difficulties by use of a permanent backing layer of greater stiffness and resistance to abrasion, then a further problem is introduced, namely, such backing layer would materially alter the vapor transport rate of the dressing and might not allow any vapor transport. If an opaque covering, such as a cloth bandage, be placed over the film to occlude the distressing view of the wound from the patient, then the disadvantage is introduced in that an attending physician must remove the cloth covering in order to view the wound.

SUMMARY OF THE INVENTION

The aforementioned problems are overcome and other advantages are provided by a thin dressing which, in accordance with the invention, is fabricated of a thin film of polyurethane or other similar elastomeric polymer or copolymer having an adhesive layer on one surface and a nonwoven fabric secured to the opposite surface. The composite structure of adhesive layer, film and nonwoven fabric is permeable to water vapor and has a sufficiently high transport rate of the vapor to permit the skin of a patient receiving the dressing to aspirate water vapor normally through the dressing. The film and the adhesive layer are transparent. The nonwoven fabric is opaque, and is constructed as a spun-bonded elastic material. Alternatively, the nonwoven fabric may also be constructed as a highly perforated elastic film of material similar to the foregoing thin film, the large amount of perforation permitting the transport of water vapor without adding any significant resistance to the vapor flow. The nonwoven elastic fabric has an extensive amount of voids passing completely through the fabric which allows passage of both liquid water and water vapor. However, the thin film is impervious the the liquid water so that the presence of spun-bonded material in no way reduces the protective barrier of the thin film to infection. The nonwoven fabric has recoverable elastic strain at least double the unstrained length, the elasticity and recoverability being multidimensional so as to be conformable to body contours and provides unhindered full range of motion on joints of a patient wearing the dressing.

It is an object of the invention to facilitate use of the dressing by an attending physician. It is a further object of the invention to reduce distress and introduce a measure of comfort to a patient wearing the dressing.

Use by an attending physician is facilitated by virtue of an inherent stiffness to the nonwoven fabric, which stiffness overcomes the tendency of the thin film to curl upon itself, the nonwoven fabric enabling the physician to readily manipulate the dressing for emplacement upon a wound. An elastic nonwoven fabric stretches along with the elastic film during positioning on the patient. A release sheet covers the adhesive layer until emplacement of the dressing upon the wound, at which time the release sheet is removed to expose the adhesive layer to the patient's skin. If desired, a gauze pad, foam or other absorptive device may be included within the dressing, the absorptive pad being positioned on the adhesive side of the film. The foregoing multiple laminate structure of the dressing is readily packaged, dispensed, and manipulated in a hospital situation.

The nonwoven fabric is bonded to the film by a fusing or by use of an adhesive. Such bonding retains the vapor transport characteristic of the dressing. The dressing may be constructed in a manner which allows the physician to view the wound without removal of the dressing. This is accomplished in one embodiment of the invention by the construction of a window in the fabric, and by adhesively securing a further layer of fabric over the window to act as a shade for opening and closing the window, thereby to show or hide the wound. Alternatively, the surface of the film facing the fabric may be provided with a release coat permitting an adhesively secured fabric to be retracted away from the film for viewing the wound, after which the fabric is restored to its original position upon the film. In the window-shade construction, a release coat may be placed on the outer surface of the fabric to facilitate lifting and replacement of the window shade.

In the use of the dressing on young children, children can be comforted in the distressing situation of a bodily wound by imprinting a colored likeness of a cartoon, animal, or other character upon the fabric. The shape of the final dressing may follow the contour of the imprint.

It is also noted that the nonwoven elastic fabric itself, due to its elasticity, its elastic recoverability, and its capacity for allowing skin to breathe, can be used as an elastic bandage, as for binding a sprained joint. The fabric can be much thinner than currently employed woven or knitted fabrics for this purpose and still retain adequate strength for use in binding sprained joints. This is particularly advantageous in the case of a binding of a sprained ankle because the fabric is thin enough to be worn within a shoe.

The elastic properties of the nonwoven material can also be employed for fabricating an elastic bandage. Since the nonwoven material is in the nature of a plastic such as polyurethane, which, while being transmissive to sweat does not absorb sweat, increased comfort to a wearer of the bandage is attained by flocking the nonwoven material with particles of a material such as cotton or rayon which absorbs sweat. The permeability of the nonwoven material to moisture absorbed by the cotton or rayon prevents excessive buildup of moisture in the flocking so as to maintain the comfortably dry feeling to the wearer.

BRIEF DESCRIPTION OF THE DRAWING

The aforementioned aspects and other features of the invention are explained in the following description, taken in connection with the accompanying drawing wherein:

FIG. 6 shows a dressing formed as bandage which can be dispensed by a child, a periphery of the nonwoven fabric extending beyond the periphery of the film and being shaped in the form of a cartoon wherein nonwoven fabric extends beyond the perimeter of the film;

FIG. 7 is an enlarged fragmentary sectional view showing an edge of the dressing in an embodiment wherein the nonwoven fabric is fused to the film;

FIG. 8 shows the view of FIG. 7 under conditions wherein the nonwoven fabric is being abraided by a pointed object such as a hairpin, FIG. 8 including a diagrammatic representation of lines of stress to demonstrate the distribution of stress about a large surface region of the film;

FIG. 9 is an enlarged fragmentary view of a dressing employing a multiply perforated plastic sheet as the nonwoven fabric;

FIG. 10 shows a construction of an electrode suitable for adhesion to a human body for measurement of body functions, the electrode being formed of electrolyte absorbing material in combination with a layer of nonwoven material; and FIG. 11 shows a sectional view of a bandage structure in which nonwoven fabric secures a gauze pad to skin.

DETAILED DESCRIPTION

Figure 1:
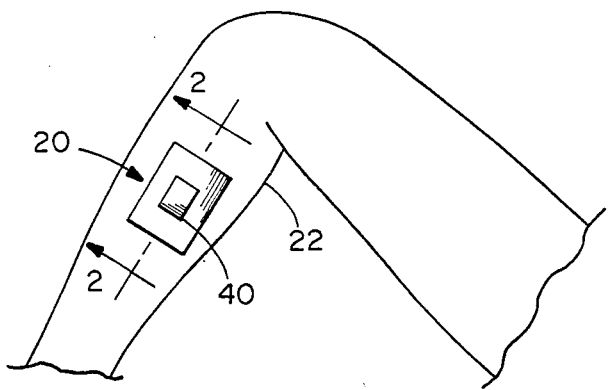
FIG. 1 shows a stylized view of a portion of a person's arm having a dressing thereon, the dressing being constructed in accordance with the invention.
Figure 2:
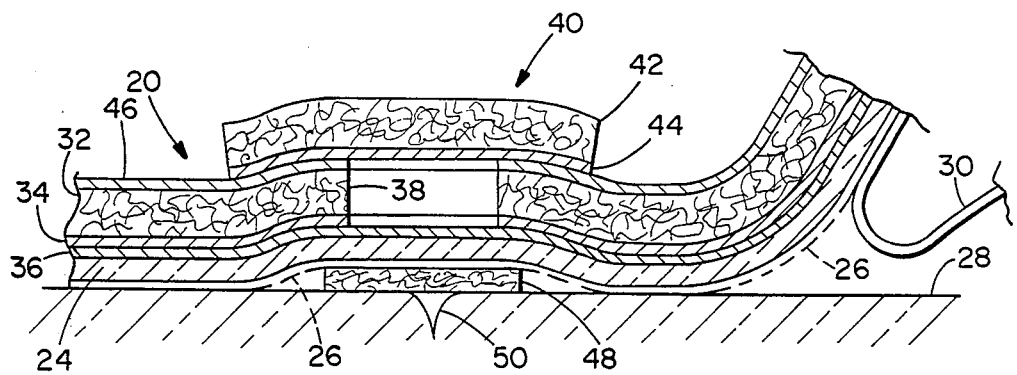
FIG. 2 shows a cross-sectional view of the dressing taken along the line 2—2 in FIG. 1.

With reference to FIGS. 1 and 2, a dressing 20 is applied to an arm 22 of a patient. The dressing 20 is constructed in accordance with the invention, and includes a film 24 having a first adhesive layer 26 for securing the dressing 20 to skin 28 of the patient. The dressing 20 is provided with a release sheet 30 such as siliconized paper which covers the adhesive layer 26 prior to use of the dressing 20. The release sheet 30 is shown partially removed in FIG. 2, such removal being accomplished to expose the adhesive layer 26 during emplacement of the dressing 20 upon the patient's arm 22.

The dressing 20 further comprises a layer 32 of fabric which, in a preferred embodiment of the invention, is formed of a sheet of nonwoven elastic material such as a spun-bonded material or a multiply perforated sheet of plastic. The fabric layer 32 is bonded to a second surface of the film 24 opposite the first adhesive layer 26 by fusing or, as shown in FIG. 2, by a second layer 34 of adhesive. The second surface of the film may be provided with a release coat 36 which cooperates with the second adhesive layer 34 to facilitate partial or complete removal of the fabric to enable a physician attending the patient to view the portion of the skin 28 covered by the dressing 20. After such viewing, the fabric is returned to its position on the film 24 and held in that position by the second adhesive layer 34.

The dressing 20, as described so far, constitutes a first embodiment of the invention which is capable of protecting an area of the skin from infection, and which permits a viewing of the region of the skin beneath the dressing 20 by releasably securing the fabric to the film 24 by an attending physician. The fabric layer 32 is opaque so as to hide the wound, skin and any discoloration or exudate which may be produced by the patient.

By way of further embodiment of the dressing 20, a window 38 can be formed within the fabric layer 32 by cutting away a portion of the fabric layer 32 having the desired shape, typically round or square, of the window 38. The window 38 permits a viewing of the skin without removal of the layer of fabric layer 32. In order to protect the portion of the film 24 bounded by the window 38, and to close off the window 38 from a viewing by the patient, a window shade 40 is removeably secured about the window 38. The shade 40 comprises a flap 42 of the fabric and a third adhesive layer 44 which secures the shade 40 to the top surface of the fabric layer 32. The top surface of the fabric layer 32 may be provided with a release coat 46 to facilitate removal of the shade 40, and to permit the shade 40 to be replaced and secured by the adhesive layer 44 to the fabric layer 32.

By way of further embodiment, a gauze pad 48 of cotton or other absorbent material may be secured to the first side of the film 24 for absorbing exudate from a wound 50 in the skin 28. The window 38 permits a viewing of the pad 48 so as to determine how much oozing of body fluids may have occurred at the site of the wound 50.

Figure 3:
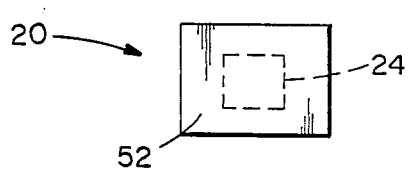
FIG. 3 shows a plan view of an embodiment of the dressing wherein nonwoven fabric extends beyond the perimeter of the film.
Figure 4:
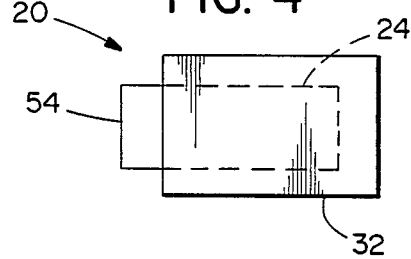
FIG. 4 shows an embodiment of the invention wherein a part of the film protrudes as a tab from underneath the nonwoven fabric.

FIGS. 3 and 4 show further configurations of the dressing 20. In FIG. 3, the fabric 32 extends beyond the periphery of the film 24 to provide a border 52 which completely surrounds the film 24. This configuration is useful as a bandage which can be applied by a child to cover a wound. In the dressing 20 of FIG. 4, the film 24 is provided with a tab 54 which extends beyond an edge of the fabric 32. This facilitates a separation of the fabric 32 from the film 24 when it is desired to lift a portion of the fabric 32 for viewing the wound 50 or gauze pad 48.

Figure 5:
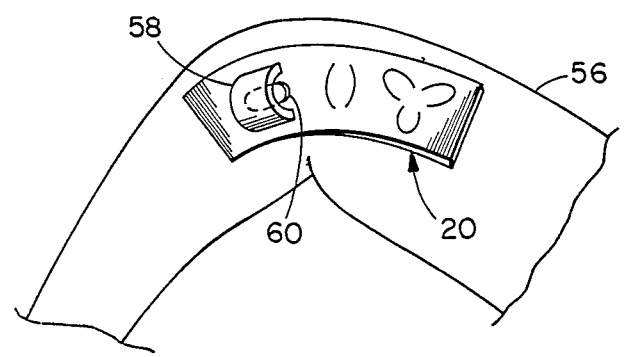
FIG. 5 shows a dressing in the form of a bandage with a cartoon sketched thereon, the cartoon showing a face wherein a mouth is placed at a point of flexure on a knee of a patient's leg to show an opening of the mouth when the leg is flexed, and wherein nonwoven fabric extends beyond the perimeter of the film.

With reference to FIG. 5, a feature of the invention is demonstrated by placing the dressing on a knee 56 of the patient. Therein, the fabric 20 is provided with a cartoon character printed directly on the surface of the fabric 32. Such a character is an aid to cheering children who may have undergone a surgical procedure and, by reducing mental stress associated with the recovery process, aids a return to good health. A particular feature of the cartoon embodiment of the dressing 20 is the emplacement of a mouth of the cartoon face at a point of flexure of the knee 56 so that, upon a bending of the knee 56, the mouth is stretched so as to appear to open. When the knee is brought to a straight position, the mouth appears to close. This is a useful feature, particularly in the case of young children, for enabling some measure of happiness to be introduced into their lives.

If desired, a pocket 58 can be created on the front surface of the fabric 32 by use of an additional layer of the fabric which is adhesively secured at edges thereof to the layer of fabric 32. A miniaturized music or sound-producing device 60 in the form of a button is placed within the pocket 58. Alternatively, in lieu of the music device 60, a sponge (not shown) of similar button shape may be placed within the pocket 58, the sponge, or other pad of liquid absorbent material, being saturated with a gel of a medicine which can be administered by contact with the skin of a patient. Liquid containing the medicine slowly passes from the sponge via the moisture permeable dressing 20 to the skin of the patient. If desired, the rate of passage of the medicine can be increased by cutting away a portion of the dressing 20 within the pocket 58. The dressing with the sponge-like material in the pocket 58 may be regarded as a transdermal medication patch useful for the slow administration of a drug such as nitroglycerin.

In FIG. 6, the cartoon aspect of the dressing 20 is embellished still further by extending the fabric of the layer 32 well beyond the perimeter of the film 24, and but cutting the outer edge of the fabric to have the physical shape of a cartoon character. As used herein and in the claims, the term "cartoon" is not limited to only the facial configuration, but is intended to include shapes of other objects frequently found in children's literature, such as, rainbows, bells, and stars. Such a form 62 having an animal face and long ears is shown in FIG. 6. In addition, an outline of facial features is imprinted on the surface of the fabric to add further realism to the cartoon form 62.

FIGS. 7 and 8 show an enlarged fragmentary view of an edge of a dressing 20 in accordance with the first embodiment of the invention comprising only the film 24 and the fabric 32 which serves as a protective layer for the film 24. In the structure disclosed in FIGS. 7 and 8, the fabric layer 32 is bonded to the film 24 by fusing, a region 64 of the fusing being indicated in FIG. 7.

FIG. 9 shows a construction of a dressing 70 having a fabric 72 formed of a sheet 74 of plastic having numerous apertures 76 extending through the sheet 74. the sheet 74 is elastomeric and, with the apertures 76, has physical characteristics similar to those of the fabric 32 of the dressing 20 in FIG. 2. In FIG. 9, the fabric 72 is bonded to the film 24 in the same fashion as has been described above for the bonding of the fabric 32 to the film 24. There follows an analysis of the dressing 20 which is understood to apply also to the dressing 70.

It is noted that the nonwoven material of the fabric layer 32 has sufficient elasticity to permit abrasion by a pointed object, such as a hair pin 66, as shown in FIG. 8. The fabric layer 32 distorts under stress of the hair pin 66 while distributing stress lines 68 about a region of the film 24 which is substantially larger than the region of contact of the hair pin 66 with the fabric layer 32. In the preferred construction of the dressing 20, the nonwoven material of the fabric layer 32 is spun-bonded. Spun-bonded material has a substantially larger capacity to absorb deformation from an abraiding object than does the film 24. Thus, an abraiding object which might will tear the film 24 is kept away from the film 24 by the fabric layer 32. Thereby, the film 24 is protected by the fabric so as to maintain integrity of the barrier against infection from bacteria. It is further noted that the distribution of the stress lines 68 about the relatively large area of the film 24 allows the film 24 to serve as a strong base for support of the fabric layer 32 in resisting the force of abrasion without any danger of tearing the film 24.

The film 24 may be of the form described hereinabove, which form is constructed of a water vapor permeable polyurethane or acrylate copolymer, or urethane and urethane copolymers as well as modified polypropylene, which film is transparent and has sufficient elasticity to be conformable to contours of a human body as well as an animal body. Typically, the film 24 has a thickness in a range of approximately 1–3 mils, though film thicknesses in the order of 0.5–10 mils may be considered. The thickness of the film in combination with the amount of voids in the plastic material of the film determine a transport rate for water vapor through the film. A transport rate greater than approximately 250 grams per square meter per 24 hour interval at a relative humidity of 80% is desired in order to insure that the skin of a patient wearing the dressing 20 can breathe properly in the sense that the water vapor discharged through the skin can permeate through the film 24 to be evaporated in air. Further details in the construction of a moisture vapor transmitting elastomeric film is disclosed in Metcalfe et al, U.S. Pat. No. 4,596,738 issued June 24, 1986. Further details in the construction of a moisture-vapor-permeable pressure-sensitive adhesive material is disclosed in Hodgson, U.S. Pat. No. 3,645,835 issued Feb. 29, 1972 and reissued as U.S. Pat. No. Re. 31,886, on May 14, 1985.

The nonwoven material of the fabric 32 is particularly advantageous over woven material because the nonwoven material can be constructed in a form which is exceedingly thin for a protective layer, typical thicknesses of the fabric layer 32 being in the range of approximately 1–30 mils, with a typical value being approximately 10 mils. The nature of the spun-bonding construction introduces a low density to the spun-bonded material, much lower than a solid form of the material, such that there are adequate voids to allow for the evaporation of water vapor from the surface of the film 24. In addition, such material has a relatively soft fluffy feel which, in combination with the great elasticity, provides for the above-noted capacity to absorb stress of an abrading object, thereby to provide for the protection of the film 24.

It is noted that spun-bonded material is employed in the practice of the invention while woven fabric is not employed. This is because available woven fabric does not have the combination of thinness, elasticity, and air permeability of the spun-bonded material. Should these characteristics become available in woven fabric in the future, then such woven fabric may be employed in the practice of the invention as an alternate component to the spun-bonded material.

An alternative form of the fabric layer 32 employs a sheet of plastic having multiple perforations in a range of typically 25–50 mils, and wherein the combined area of the apertures is in the range of 5–30%, typically 17%, of the area of the plastic sheet. This is a highly discontinuous fabric providing ample opportunity for transpiration of water vapor. It is noted that the fabric is not waterproof in the sense that liquid water can pass through the fabric. However, the waterproof characteristic is not required of the fabric layer 32 because the film 24 provides an adequate barrier to the flow of water.

The spun-bonded material is formed by a fusing or by a chemical interaction of filaments of material in a random pattern rather than by weaving or knitting strands of material, as in knitted fabric. By way of example, spun-bonded urethane is a thermal plastic polyurethane elastomer formed as a spun-bonded fabric. The fabric has a structure of three dimensional entanglement of polyurethane fine continuous or discontinuous elastic filaments which are thermally or chemically melt bonded. The fabric is characterized by being stretchable in all directions, typically in excess of two times the relaxed length. The fabric is highly permeable to air because of the thinness of the fine filament structure, the filaments of the structure being randomly webbed and bonded only at their intersections to define interstices. The thickness of the fabric is in a range of typically 0.05–0.75 millimeters. The density of the fabric is in a range of typically 15–250 grams per square meter.

The second and the third adhesive layers 34 and 44 are solvent-based acrylic aerated adhesive layer having a thickness on the order of one mil. Permeability to water vapor may be increased by flash heating to sputter out the solvent vehicle which carries the adhesive particles, the sputtering leaving voids in the adhesive which facilitate transport of water vapor through a layer of the adhesive.

The release coat, applied to the upper surface of the film 24, and the release coat applied to the upper surface of the fabric layer 32 are formed, preferably, as a silicone-based coating. If desired, the coating may be fused to the underlying substrate of film 24 or layer 32 by heat. Such release coats may be cured by bombardment with an electron beam or by treatment with an ultraviolet beam.

In a further aspect of the invention, it has been found that the fabric layer 32, by itself, has sufficient tensile strength to be used as an elastic bandage for binding wounds, such as a sprained ankle, or other sprained joint. A spun-bonded material, such as a polyurethane spun-bonded material, is transmissive to sweat without absorbing the sweat. Increased comfort to a person wearing the elastic bandage is attained by providing material which absorbs the sweat. This is accomplished, in accordance with another aspect of the invention by applying a sweat-absorbent material such as cotton or rayon particles by a flocking of the particles on the spun-bonded material. The flocking process comprises a spraying of both an adhesive and the particles of cotton or rayon on the spun-bonded material, the adhesive securing the flocked particles on the spun-bonded material. Sufficient comfort is provided to the wearer of the bandage by flocking only the side of the bandage which faces the skin of the wearer. Also, if desired, the cartoon characters can be imprinted on the material of the elastic bandage. Also, the printing of other indicia on the elastic bandage can be accomplished in a compressed format such that, upon a stretching of the bandage during a binding of a wound, the indicia expand to the desired proportions to indicate a proper amount of tension in the elastic bandage.

The use of nonwoven material is, furthermore, distinctly advantageous over the use of woven material because the nonwoven material can be constructed as a much thinner sheet which allows flexing of the film 24 without introduction of unnecessary stress as might occur when a thin film of material is bent around a thick layer of material, as would occur if woven material were used as the protective layer. By use of two very thin layers, each having a thickness on the order of one mil as is the case with the disclosed film 24 and fabric layer 32, the resultant dressing has the flexibility and conformability of the layer of skin which is covered by the dressing 20. By considering this conformability characteristic in combination with the capability to breathe, to resist liquid water, and to exclude infectious agents, the dressing 20 may well be regarded as a synthetic skin. It is also noted that, in view of the secure adhesive bond between the film 24 and the skin 28 of the patient, the film and skin can be regarded as a composite structure which serves as a foundation for support of the protective layer 32 of fabric. This is an important part of the protective mechanism which, as noted above with reference to FIG. 8, provides that the protective layer deforms more readily in response to an abrasive force than does the composite structure of the film and the skin. There results the distribution of the abrasive forces about the composite structure of the film and skin to reduce the magnitude of such force at any one point on the film, thereby to inhibit a tearing of the film. In this respect, the dressing 20 has a further characteristic of skin in that the fabric 32 may be likened to the epidermis which protects the dermis from abrasive forces.

FIG. 10 shows the construction of a flexible electrode assembly 78 which is secured adhesively to the skin 80 of a patient, the electrode assembly 78 being formed of a layer 82 of nonwoven fabric such as the layer 32 of FIG. 2 so as to be moisture permeable and comfortable for wearing by the patient. A flexible sponge 84 or similar liquid absorbent material is enclosed by a flexible elastomeric cap 86 which is fused to the layer 82 for securely holding the sponge 84 in place. The cap 86 may be formed of the same material as the layer 82. An aperture 88 is disposed within the layer 82, and centered beneath the sponge 84. An electrode wire 90 passes through the cap 86 to make contact with the sponge 84, the wire 90 being secured to the cap 86 by fusing of the cap material about the wire 90.

In operation, the sponge 84 contains a gel of electrolyte which provides an electrically conductive path between the wire 90 to the skin 80, the electrolyte making contact with the skin 80 via the aperture 88. The elastomeric properties of the nonwoven material of the layer 82 and of the cap 86, wherein recoverable stretch may be as much as 100% in three dimensions allows the electrode assembly 78 to conform to undulations in the skin 80 and to distend with movement of the patient. This permits a much more secure holding of the electrode assembly 78 to the skin 80 of the patient. In addition, the moisture-permeable and air-breathable qualities of nonwoven fabric, particularly spun-bonded fabric, in combination with the extreme thinness of the fabric insure comfort in the wearing of the electrode 78. The wire 90 is readily connected to electronic measurement circuitry for use in patient monitoring situations such as an electrocardiogram, transcutaneous nerve stimulation, and an electromylogram.

FIG. 11 shows a simplified form of bandage 92 in which a gauze pad 94 is secured by a layer 96 of spun-bonded fabric to the surface of skin 98, which skin may be the skin of a human or an animal. The gauze pad 94 serves to absorb exudate from a wound 100 in the skin 98 and to protect the wound 100 from an external environment. The gauze pad 94 is permeable to both water vapor and to air. The layer 96 is secured by an adhesive 102 to the surface of the skin 98, the adhesive 102 being disposed along the bottom surface of the layer 94. The adhesive 102 also serves to secure the pad 94 to the layer 96. The spun-bonded fabric of the layer 96 is elastomeric with three dimensional stretch, there being recoverable stretch in excess of 100% along each of the three dimensions. Open regions of the spun-bonded fabric occupy at least 30% of the total surface area of the layer 96. Thickness of the layer 96 is in the range of 0.05 to 0.75 millimeters. These characteristics of the spun-bonded fabric give the layer 96 the capacity to conform to undulations of the skin 98, including a stretching of the skin in the situation wherein the skin covers a limb which is being bent such as at a knee or elbow. In addition, the open spaces or voids within the fabric provides sufficient air permeability for increased comfort to the person wearing the bandage. Since the bandage 92 does not include the film 24 of FIG. 2, the bandage 92 of FIG. 11 is to be employed only in those situations, such as mild skin irritations and/or mild wounds in which external moisture is not a hazard, and wherein the amount of exudate from the wound 100 is sufficiently small so as to be totally absorbed by the pad 94.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

What is claimed is:

1. A moisture-vapor-permeable dressing for use on human and animal skin comprising:
a conformable elastomeric film to be placed on the skin, the film being permeable to water vapor but impermeable to liquid water;
an adhesive disposed as a breathable layer along a first surface of said film for securing said film to the skin; and
a protective layer of conformable elastomeric fabric of nonwoven filamentary material bonded to a second surface of said film opposite said first surface to form therewith a composite laminated structure, said protective layer of nonwoven material having a discontinuous form open to a transpiration of water vapor at a rate substantially greater than the permeability of said film, said protective layer of nonwoven material having a multidimensional recoverable elastic strain at least double an unstrained length of the material so as to be conformable to a human or animal body; and wherein
said protective layer deforms more readily, in response to an abrasive force, than does a composite structure comprising said film, said adhesive and the skin secured by the adhesive to said film thereby to distribute an abrasive force over the composite structure to inhibit tearing of said film.

2. A dressing according to claim 1 further comprising a release sheet removably securable to said first surface of said film, for detachment from said adhesive prior to application of said dressing to the skin.

3. A dressing according to claim 1 further comprising a second layer of a breathable adhesive, said protective layer being bonded to said second surface of said film by said second layer of adhesive.

4. A dressing according to claim 1 wherein said film is transparent and a portion of said protective layer is cut away to form a window for viewing skin beneath said film.

5. A dressing according to claim 4 further comprising a section of protective layer material adhesively securable about said window as a window shade for occluding a view of skin beneath the window.

6. A dressing according to claim 1 wherein said protective layer is fused to the second surface of said film.

7. A dressing according to claim 1 further comprising absorptive pad means secured to said film at a portion of said first surface for absorbing exudate from the skin.

8. A dressing according to claim 1 wherein said protective layer extends beyond a perimeter of said film.

9. A dressing according to claim 8 further comprising absorptive pad means secured to said film at a central portion of said first surface for absorbing exudate from the skin.

10. A dressing according to claim 1 wherein said nonwoven material is spun-bonded.

11. A dressing according to claim 1 wherein said nonwoven material is spun-bonded urethane.

12. A dressing according to claim 1 wherein said nonwoven material is a perforated sheet of plastic material.

13. A dressing according to claim 1 wherein a periphery of said nonwoven material is formed in the shape of a cartoon-type of image.

14. A dressing according to claim 1 wherein the nonwoven material is imprinted with a cartoon-type of image.

15. A dressing according to claim 14 wherein a periphery of said nonwoven material is formed in the shape of a cartoon-type of image.

16. A dressing according to claim 15 further comprising:
- an additional layer of nonwoven material placed over a portion of an outer surface of the dressing to form a pocket; and
- a miniaturized music device held within said pocket.

17. A dressing according to claim 1 further comprising an additional layer of nonwoven material placed over a portion of an outer surface of the dressing to form a pocket, said pocket being suitable for holding a sound-producing device.

18. A dressing according to claim 1 wherein a part of said film extends beyond an edge of said nonwoven material to form a tab.

19. A dressing according to claim 1 wherein said nonwoven material extends beyond a periphery of said film to form a border enclosing said film.

20. A moisture-vapor-permeable dressing for use on human and animal skin comprising:
- a conformable elastomeric film to be placed on the skin, the film being permeable to water vapor but impermeable to liquid water;
- a breathable adhesive disposed as a layer along a first surface of said film for securing said film to the skin, said film with said adhesive together having a moisture-vapor-permeability greater than approximately 250 grams per square meter per 24 hour interval of time at a relative humidity of 80%; and
- a protective layer of conformable elastomeric fabric of nonwoven material bonded to a second surface of said film opposite said first surface to form therewith a composite laminated structure, said protective layer of nonwoven material having a discontinuous form open to a transpiration of water vapor at a rate substantially greater than the permeability of said film to provide said laminated structure with a rate of water vapor transpiration essentially the same as that of said film with said adhesive; and wherein
- said protective layer deforms more readily, in response to an abrasive force, than does a composite structure comprising said film, said adhesive and the skin secured by the adhesive to said film, thereby to distribute an abrasive force over the composite structure to inhibit tearing of said film; and
- further comprising a second layer of a breathable adhesive, said protective layer being bonded to said second surface of said film by said second layer of adhesive; and
- wherein said second layer of adhesive is disposed on a surface of said protective layer, there being a release coat on the second surface of said film for releasing at least a part of said protective layer from said film without disconnection of said film from the skin, said film being transparent to permit a viewing of skin beneath said dressing.

21. A moisture-vapor-permeable dressing for use on human and animal skin comprising:
- a conformable elastomeric film to be placed on the skin, the film being permeable to water vapor but impermeable to liquid water;
- a breathable adhesive disposed as a layer along a first surface of said film for securing said film to the skin, said film with said adhesive together having a moisture-vapor-permeability greater than approximately 250 grams per square meter per 24 hour interval of time at a relative humidity of 80%; and
- a protective layer of conformable elastomeric fabric of nonwoven material bonded to a second surface of said film opposite said first surface to form therewith a composite laminated structure said protective layer of nonwoven material having a discontinuous form open to a transpiration of water vapor at a rate substantially greater than the permeability of said film to provide said laminated structure with a rate of water vapor transpiration essentially the same as that of said film with said adhesive; and wherein
- said protective layer deforms more readily, in response to an abrasive force, than does a composite structure comprising said film, said adhesive and the skin secured by the adhesive to said film, thereby to distribute an abrasive force over the composite structure to inhibit tearing of said film; and
- wherein said second layer of adhesive is disposed on a surface of said protective layer, there being a release coat on the second surface of said film for releasing at least a part of said protective layer from said film without disconnection of said film from the skin, said film being transparent to permit a viewing of skin beneath said dressing;
- a portion of said protective layer is cut away to form a window for viewing skin beneath said film; and
- said dressing further comprises a second of protective layer of material adhesively securable about said window as a window shade for occluding a view of skin beneath the window.

22. An elastic bandage formed of a strip of nonwoven filamentary material, said nonwoven material being a spun-bonded elastomer, said nonwoven material having a multidimensional recoverable elastic strain at least double an unstrained length of the nonwoven material to be conformable to a patient's body, there being a flocking of water-absorbent material secured to a surface of the nonwoven material.

23. An elastic bandage according to claim 22 wherein said material is imprinted with a design which extends upon a stretching of the bandage during application of the bandage to a limb of a person, the appearance of the design being indicative of a desirable amount of stretching.

24. A moisture-vapor-permeable dressing for use on human and animal skin comprising:

a conformable elastomeric film to be placed on the skin, the film being permeable to water vapor but impermeable to liquid water;

a breathable adhesive disposed as a layer along a first surface of said film for securing said film to the skin, said film with said adhesive together having a moisture-vapor-permeability greater than approximately 250 grams per square meter per 24 hour interval of time at a relative humidity of 80%; and a protective layer of conformable elastomeric fabric of nonwoven material bonded to a second surface of said film opposite said first surface to form therewith a composite laminated structure, said protective layer of nonwoven material having a discontinuous form open to a transpiration of water vapor at a rate substantially greater than the permeability of said film to provide said laminated structure with a rate of water vapor transpiration essentially the same as that of said film with said adhesive; and wherein said protective layer deforms more readily, in response to an abrasive force, than does a composite structure comprising said film, said adhesive and the skin secured by the adhesive to said film, thereby to distribute an abrasive force over the composite structure to inhibit tearing of said film; and said dressing further comprises an additional layer of nonwoven material placed over a portion of an outer surface of the dressing to form a pocket, there being means within said pocket for dispensing a liquid medicine via said permeable film to be absorbed by said skin.

25. A surgical dressing comprising:

a conformable elastomeric film permeable to water vapor but impermeable to liquid water;

a protective layer of conformable elastomeric fabric bonded to said film to form therewith a laminated structure, said protective layer of fabric having a multidimensional recoverable elastic strain at least double an unstrained length of the fabric to be conformable to a patient's body; and adhesive means disposed along said film on a side opposite said protective layer for securing said dressing to the flesh of a patient, and wherein said laminated structure together with said adhesive means are permeable to water vapor, said laminated structure being sufficiently elastic to conform to contours of the patient's flesh; and wherein said protective layer is opaque, the bonding of said protective layer to said film providing for a releasable securing of said protective layer to said film to permit a viewing of the flesh.

26. A dressing according to claim 25 having a construction in the form of a cartoon character.

27. A surgical dressing comprising:

a conformable elastomeric film permeable to water vapor but impermeable to liquid water;

a protective layer of conformable elastomeric fabric bonded to said film to form therewith a laminated structure, said protective layer of fabric having a multidimensional recoverable elastic strain at least double an unstrained length of the fabric to be conformable to a patient's body; and adhesive means disposed along said film on a side opposite said protective layer for securing said dressing to the flesh of a patient, and wherein said laminated structure together with said adhesive means are permeable to water vapor, said laminated structure being sufficiently elastic to conform to contours of the patient's flesh; and wherein said protective layer deforms more readily in response to an abrasive force than does a composite structure comprising said film, said adhesive and the skin secured by the adhesive to said film, thereby to distribute an abrasive force over the composite structure to inhibit tearing of said film.

28. A dressing according to claim 27 having a construction in the form of a cartoon character.

29. A breathable surgical dressing comprising:

a conformable elastomeric film permeable to water vapor but impermeable to liquid water;

a protective layer of conformable elastomeric fabric bonded to said film to form therewith a laminated structure; and adhesive means disposed along said film on a side opposite said protective layer for securing said dressing to the flesh of a patient, said laminated structure being sufficiently elastic to conform to the contours of the patient's body; and wherein the bonding of said protective layer to said film provides for a releasable securing of said protective layer to said film to permit a viewing of the flesh, said fabric comprising filaments of elastomeric material arranged to form openings for transpiration of water vapor, the fabric having a density in the range of approximately 15–250 grams per square meter and a thickness in the range of approximately 0.05–0.75 millimeters.

30. A breathable surgical dressing comprising:

a conformable elastomeric film permeable to water vapor but impermeable to liquid water;

a protective layer of conformable elastomeric fabric bonded to said film to form therewith a laminated structure, said protective layer of fabric having a multidimensional recoverable elastic strain at least double an unstrained length of the fabric to the conformable to a patient's body; and adhesive means disposed along said film on a side opposite said protective layer for securing said dressing to the flesh of a patient, said laminated structure being sufficiently elastic to conform to the contours of the patient's body; and wherein said protective layer deforms more readily in response to an abrasive force than does a composite structure comprising said film, said adhesive and the skin secured by the adhesive to said film, thereby to distribute an abrasive force over the composite structure to inhibit tearing of said film, said fabric comprising filaments of elastomeric material arranged to form openings for transpiration of water vapor, the fabric having a density in the range of approximately 15–250 grams per square meter and a thickness in the range of approximately 0.05–0.75 millimeters.

* * * * *